United States Patent

Mills

(10) Patent No.: US 8,795,213 B2
(45) Date of Patent: Aug. 5, 2014

(54) SPINAL ORTHOSIS

(75) Inventor: Andrew James Mills, Chesterfield (GB)

(73) Assignee: The Spinecorporation Limited, Chesterfield (GB)

( * ) Notice: Subject to any disclaimer, the term of this patent is extended or adjusted under 35 U.S.C. 154(b) by 123 days.

(21) Appl. No.: 12/698,316

(22) Filed: Feb. 2, 2010

(65) Prior Publication Data

US 2010/0217166 A1    Aug. 26, 2010

(30) Foreign Application Priority Data

Feb. 24, 2009  (GB) .................................. 0903093.3

(51) Int. Cl.
*A61F 5/02* (2006.01)
*A61F 5/37* (2006.01)

(52) U.S. Cl.
USPC ............. 602/19; 128/869; 128/874; 128/875; 128/876; 2/44

(58) Field of Classification Search
USPC ............ 602/19; 128/98.1, 99.1, 100.1, 101.1, 128/874–876, 869; 2/44, 45, 23, 308–309
See application file for complete search history.

(56) References Cited

U.S. PATENT DOCUMENTS

| | | | | |
|---|---|---|---|---|
| 4,789,372 A | * | 12/1988 | Wicks | 450/155 |
| 5,464,136 A | * | 11/1995 | Eddy | 224/666 |
| 5,599,286 A | * | 2/1997 | Labelle et al. | 602/19 |
| 2006/0282032 A1 | * | 12/2006 | Smith et al. | 602/19 |

FOREIGN PATENT DOCUMENTS

| | | |
|---|---|---|
| AT | 009 563 U2 | 12/2007 |
| EP | 0 153 237 A2 | 8/1985 |
| EP | 0 735 847 | 6/1995 |
| ES | 2 294 890 B1 | 4/2008 |
| WO | 95/17142 | 6/1995 |
| WO | 2004/019812 A2 | 3/2004 |
| WO | 2007/043079 A1 | 4/2007 |

OTHER PUBLICATIONS

The Spinecorporation Limited; "SpinCor Brace"; www.spinecorporation.com/English/index.htm; 2002.
The Spinecorporation Limited; "The SpineCor Dynamic Corrective Brace: SpineCor System Overview and Treatment Results"; Jan. 2007.
Combined Search and Examination Report which issued in connection with corresponding Great Britain Application No. 0903093.3 on Jun. 12, 2009.

* cited by examiner

*Primary Examiner* — Patricia Bianco
*Assistant Examiner* — Kari Petrik
(74) *Attorney, Agent, or Firm* — Harness, Dickey & Pierce, P.L.C.

(57) ABSTRACT

An orthosis for the treatment of congenital, developmental and degenerative spinal deformities or misalignments, including an upper thoracic component adapted to cover part or the whole thorax and made in non-elastic material, a pelvic component adapted to encircle the pelvis and made in elastic-material and reinforced with non-elastic materials, a non-elastic strapping system adapted to encircle the pelvis transversely and providing a stable fitting, resistant to transverse plane rotations and proximal migration, and at least four removable, corrective elastic bands running obliquely around part or all of the body circumference and attach from the thoracic component (right shoulder, left shoulder, right distal thorax, left distal thorax) to posterior-lateral and/or anterior sections of the pelvic component.

8 Claims, 2 Drawing Sheets

SPINAL ORTHOSIS

This application claims the benefit of British Application Serial No. 0903093.3 filed 24 Feb. 2009

FIELD OF THE INVENTION

This invention relates to an orthosis for the non-operative orthotic treatment of spinal deformities including scoliosis, hyper-kyphosis and spinal misalignments.

BACKGROUND OF THE INVENTION

In EP0735847 is described an orthosis for the treatment of scoliotic deformities in children, and comprising basically an upper thoracic attachment means and a lower pelvic, attachment means with semi-elastic means adapted to be anchored at upper and lower parts thereof respectively to said upper and lower attachment means and to extend substantially obliquely intermediate said upper and lower attachment means. The function of the semi-elastic means is to exert derotational forces on the thoracic and lumber spines of the user in opposite directions. Whilst this orthosis has been used successfully for a number of years its design, as indicated above, was for children, where correction of a problem was an objective although fitting results in a mobility problem for the user.

OBJECT OF THE INVENTION

A basic object of the present invention is to provide an orthosis of the general type described in EP0735847, but which is not primarily intended for juvenile use, but which is capable of providing spinal pain relief and/or postural realignment and/or correction of deformity, particularly for adults.

SUMMARY OF THE INVENTION

According to the present invention, there is provided an orthosis (100) for the treatment of congenital, developmental and degenerative spinal deformities or misalignments, comprising
(i) an upper thoracic component (101) adapted, in use, to cover part or the whole thorax and made in non-elastic material,
(ii) a pelvic component (110) adapted, in use, to encircle the pelvis and made in elastic-material and reinforced with non-elastic materials,
(iii) a non-elastic strapping system adapted, in use, to encircle the pelvis transversely as a pelvic band (111) and providing a stable fitting, resistant to transverse plane rotations and proximal migration, and
(iv) at least four removable, corrective elastic bands (130) running obliquely around part or all of the circumference of a torso and attach from the thoracic component (101) (right shoulder, left shoulder, right distal thorax, left distal thorax) (130(1)A, 130(2)A, 130(3)A, 130(4)A) to posterior-lateral and/or anterior sections of the pelvic component (130(1)B, 130(2)B, 130(3)B, 130(4)B), the corrective bands (130) being adapted, in tension and fastening position according to the specific corrective movement required, to be applied to a segment of the torso involved in order to correct the deformity, relieve pain and/or improve posture and/or prevent progression/correction of the deformity.

ADVANTAGES OF THE INVENTION

Three dimensional postural changes provoked by the corrective bands bring about the corrective movement which have 3D effects of the spine in sagital, frontal and transverse planes. Variations in band sequence, positioning, vectors and tension allow infinite variations in spinal loading at an individual vertebral level in all three planes of space.

The unique changes in spinal dynamic loading response and alignment allow for specific vertebral net loading increase or decrease either anterior, posteriorly or medio-laterally. Such changes in spinal loading may contribute towards spinal remodeling, delay in deformity progression, correction of deformity, relief of pain and/or improvement in overall posture.

The orthosis in accordance with the invention more specifically is intended primarily for the treatment of adult patients with such deformities whether they be congenital, developmental, degenerative of traumatic in origin, with the specific objectives of pain relief and/or postural correction and/or prevention of progression, spinal correction or stabilization.

The orthosis in accordance with the invention provides postural/spinal realignment using dynamic correction forces applied through the shoulders, thorax and pelvic whilst still allowing almost total mobility of the body. This postural rehabilitation approach to the treatment of spinal deformities using an orthotic device is a novel approach not seen before in this field.

Furthermore, the orthosis in accordance with the invention still allows almost complete mobility of the body contrary to any current orthosis.

In principle, the orthosis in accordance with the invention utilizes dynamic rather than passive forces and employs the principle of mirror image postural remodelling rather than conventional 3 point pressure principles (e.g. of EP0735847) to affect changes in posture, spinal shape and loading.

The orthosis in accordance with the invention also applies its forces to shoulders, thorax and pelvis without the use of pads, via the thoracic, pelvic and corrective band components.

The treatment objectives are;
Pain; reduction of patient's numerical pain scores and/or frequency of pain. Posture; improvement in postural balance and/or cosmesis.

Progression; prevention of curves progression either stabilization or improvement of spinal geometric measurements, and non-elastic strapping system encircling the pelvis transversely and providing a stable fitting, resistant to transverse plane rotations and proximal migration.

It is a further aim of the present invention to use interchangeable and adjustable modular components to allow various degrees and patterns of force application for the correction, stabilization, or changes in spinal loading required to achieve the specific treatment objective for the specific postural and/or spinal deformities and/or spinal misalignment during treatment.

Three dimensional postural changes provoked by corrective bands bring about the corrective movement which have 3D effects on the spine in sagital, frontal and transverse planes. As will be appreciated by persons skilled in the art, variations in band sequence, positioning, vectors and tension allow infinite variations in spinal loading at an individual vertebral level in all three planes of space.

The unique changes in spinal dynamic loading response and alignment allow for specific vertebral net loading or decrease either anterior, posteriorly or medio-laterally. Such changes in spinal loading may contribute towards spinal remodelling, delay in deformity progression, correction of deformity, relief of pain and/or improvement in overall posture.

Uniquely the design of the orthosis uses no rigid materials or pads to apply forces to specific locations of the patient's torso, forces are applied dynamically to the torso through the whole of the orthosis contact area with the torso encouraging postural changes, stimulating proprieoceptive feed back with repetition of movement slowing bringing about soft tissue changes, improved muscle strength and balance that result in permanent or semi-permanent changes to the patient's body posture and spinal alignment. The orthosis allows virtually full mobility of the patient during treatment due to the unique design and elastic materials used.

Preferred or Optional Features

The pelvic component is constituted by a pair of pelvic shorts. The pelvic shorts has a fastening system that allows for sizing changes within a limited range, but allows the strong pelvic band to be tensioned sufficiently to provide a stable anchorage for corrective band attachment.

BRIEF DESCRIPTION OF THE DRAWINGS

Having thus generally described the nature of the invention, reference will now be made to the accompanying drawings showing by way of a preferred embodiment thereof, in which.

DETAILED DESCRIPTION OF THE DRAWINGS

Figure 1A:
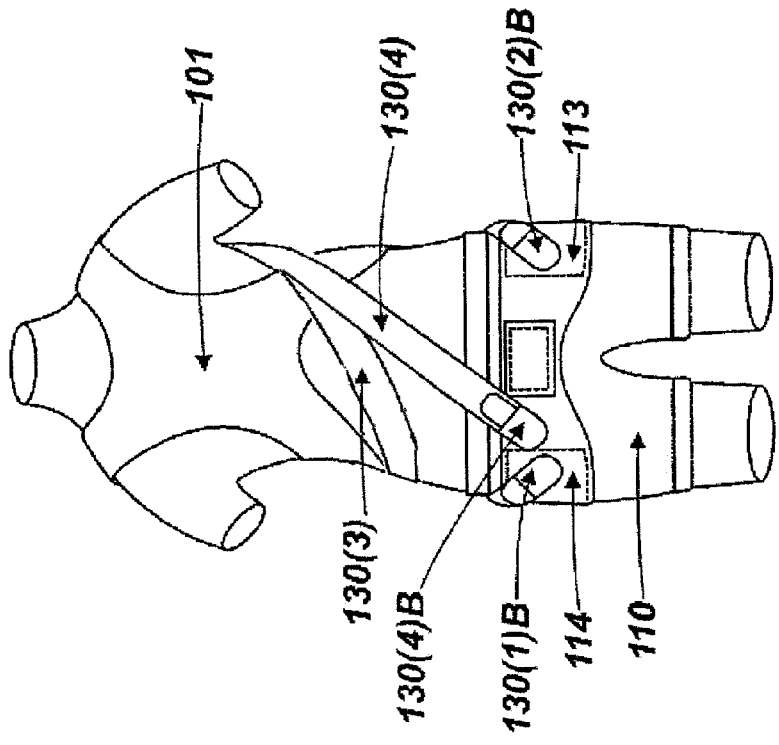
FIGS. 1a and 1b are front (anterior) and back (posterior) elevation views, respectively of the orthosis in accordance with the present invention shown on a human torso.
Figure 1B:
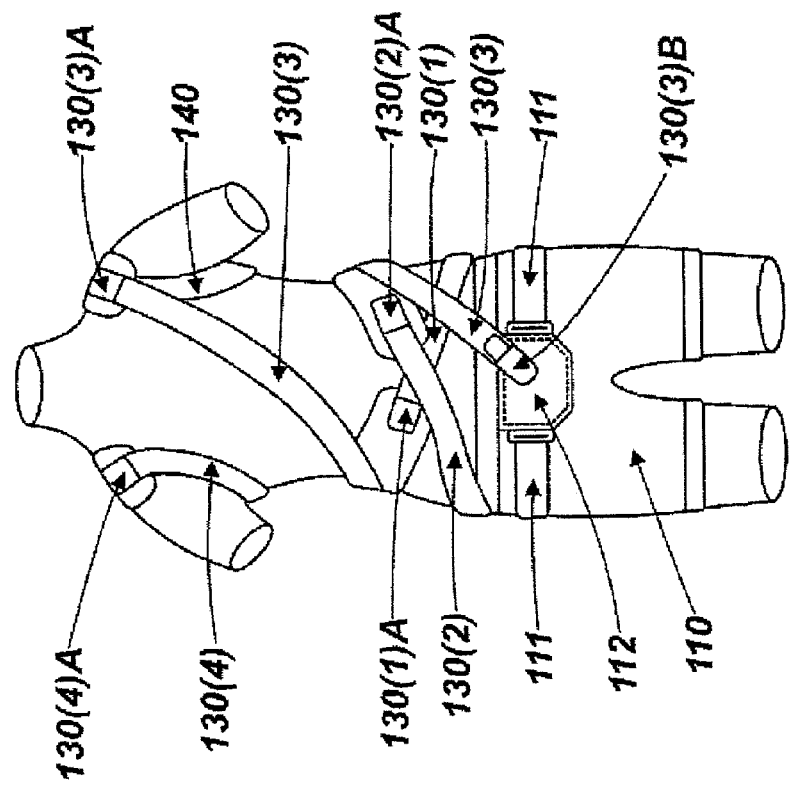
Figure 1D:
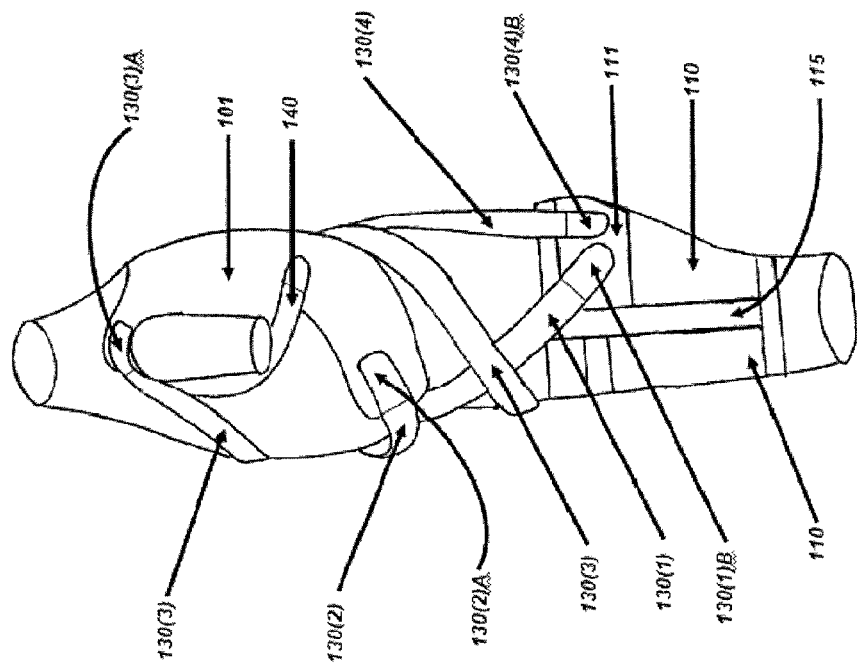
FIGS. 1c and 1d are right side (lateral) and left side (lateral) elevation views, respectively, of the orthosis in accordance with the present invention shown on a human torso.
Figure 1C:
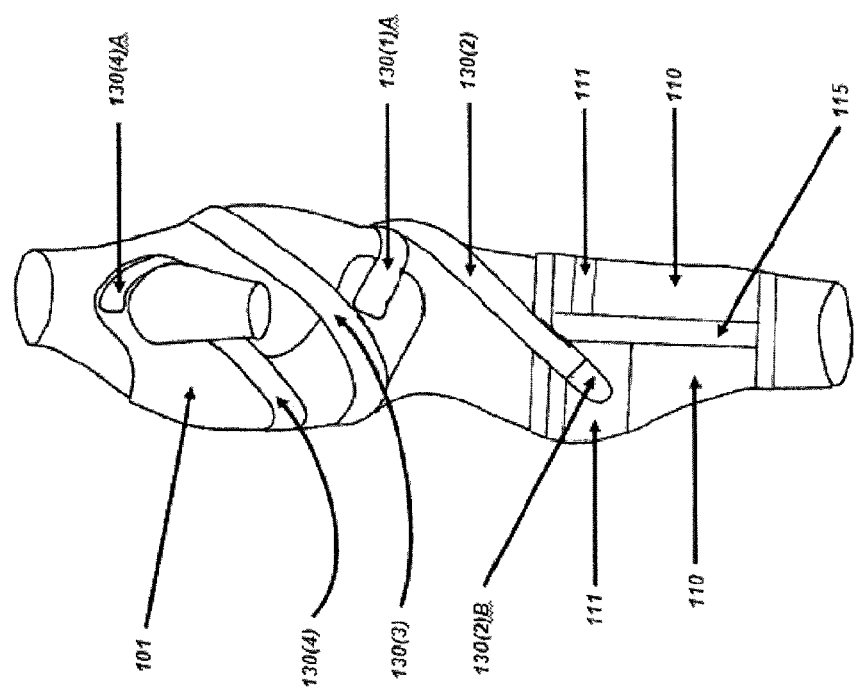

An orthosis (100) in accordance with the present invention, is intended for the treatment of flexible to rigid spinal deformities/misalignments congenital, developmental, traumatic or degenerative in origin with the objectives of pain relief, postural improvement, progression management stabilization/correction of spinal deformity/misalignment.

The single design with its modular components allows for treatment of all of the aforementioned conditions of varying severity for a wide range of patient sizes. The device is made entirely of supple elastic and non-elastic materials designed in such a way as to allow near normal mobility of the spine whilst applying the previously mentioned dynamic forces.

The orthosis (100) comprises an upper thoracic component (101), a lower pelvic component (110) and a set of corrective elastic bands (130).

The upper thoracic component (101) is made of a cotton/dracon fabric containing Velcro® loop patches on each of its four wings, right thoracic, left thoracic, right shoulder and left shoulder to which are connected by Velcro® hook patches the corrective elastic bands (130). The so-called Bolero thoracic component (101) extends posteriorly from the level of the fourth to the twelfth thoracic vertebrae with left and right lower thoracic wings passing obliquely and laterally around the lower margin or the rib cage (eleventh rib level) to the anterior of the chest. The right and left upper shoulder wings extend over each shoulder to the anterior chest approx 20-40 mm, each shoulder wing having a Velcro® loop patch for corrective band attachment. This thoracic component of supple yet non-elastic material is prefabricated in different sizes in order to accommodate not only children from approximately three years of age, adolescents but importantly adults of both sexes up to 6 foot 3 inches in height, or can be custom fabricated from a set of anthropometric measurements for subjects of unusual size of torso configuration.

The lower pelvic component (110) consists of a pair of shorts made of an elastic net material available in sizes from 20" to 50" to accommodate most children, adolescents and adult sizes. They can of course be custom fabricated from a set of anthropometric measurements for persons who cannot be accommodated in the prefabricated sizes. These elasticated shorts act as a carrier for a Velcro® non-elastic pelvic loop or band (111) encircling the entire pelvis at a level just inferior to the anterior supers iliac spines (ASIS) passing horizontally around the pelvis at the same level laterally and posteriorly. The Velcro® pelvic band (111) has broad areas of loop Velcro® for attachment of corrective bands (130) one central anterior section (112) and right (113) and left (114) posterior-lateral sections connecting with Velcro® at the centre back (posterior) with adjustment for sizing. In addition, there are two (right and left) anterior reverse pull Velcro® straps (111) connecting the anterior Velcro® panel (112) and two posterior-lateral Velcro® panels (113, 114). These serve both to tension the pelvic loop for stability of fit and size adjustment.

The pelvic band (111) is sewn to the shorts in the area of the anterior Velcro® panel (111) and laterally on the right and left posterior-lateral Velcro® panels (112, 113). The central ⅔ of the posterior Velcro® panels are secured to the elastic shorts by means of Velcro® hook and loop sections stitched to the adjoining surfaces, the Velcro® stitched directly to the shorts being elasticated to allow stretch for size adjustment.

The shorts (110) adjust to the size of the thighs only by stretch of the material. The anterior loop Velcro® panel (112) for attachment of corrective bands (130) allows for the attachment of up to two corrective bands (130). The right (113) and left (114) posterior-lateral loop Velcro® panels allow for the attachment of up to three corrective bands (130) on each side.

The elastic net material of the shorts (110) is reinforced down the lateral sides to restrict undesirable stretch in vertical length. There is an anterior opening in the crotch area of the shorts (110) to facilitate toileting and allow for unisex fitting.

The third element of the orthosis (100) is the set of corrective bands (130) typically four; however, occasionally a fifth band is added. These bands (130) are produced in a specialized elastic material that is both Velcro® receptive and allows extension of up to 40% of its original length. This level of elasticity and the strength of the elastic are important features of the design in order to provide the necessary corrective forces to the torso and ultimately the spine whilst allowing almost normal mobility. The corrective elastic bands (130) are available in four lengths 50 cm, 80 cm, 110 cm and 140 cms and two widths 30 mm and 50 mm these bands are designed to be cut to specific patient requirements during the brace fitting process. At one end of each corrective band (130) is a fixed stitched hook Velcro® patch (130(1)A, 130(2)A, 130(3)A, 130(4)A) designed to attach to the Bolero or thoracic component (101) of the orthosis (100). To the opposite end of each corrective band (130) attaches a removable Velcro® clip end (130(1)B, 130(2)B, 130(3)B, 130(4)B) which is designed to semi-permanently fix to the elastic material of the corrective band (130) after cutting to size and a "standard" hook Velcro® patch for attachment to the pelvic component (loop Velcro® sections anterior right posterior-lateral and left posterior lateral of the pelvic band).

The specific configuration of corrective bands, number, direction, tension and fastening locations are specific to the patient's deformity (scoliosis, kyphosis or spinal misalignment), and will be apparent to persons skilled in the art.

Accessories

Non-functional bands made of the same elasticated material may be added to the orthosis in order to maintain optimal positioning of the corrective bands around the patients body. One or two of these so-called comfort bands may be applied to each orthosis.

A special bodysuit or leotard has been designed to be worn as an interface garment under the orthosis, this prevents rubbing from corrective bands in sensitive areas of the body (under the arms and in the waist) as well as allowing for toileting without the need to remove the orthosis. The bodysuit/leotard is fabricated in a cotton/elastic material allowing stretch whilst maintaining a smooth wrinkle free close fit to the patient's body. There is a press fastener opening of the bodysuit/leotard between the legs to allow for toileting and ease of donning and doffing. Whilst this accessory item has no functional role it does improve comfort and prevents potential skin irritations in sensitive areas.

The invention claimed is:

1. An orthosis (100) for the treatment of congenital, developmental and degenerative spinal deformities or misalignments in a patient, comprising a thoracic Bolero component attached to a pelvic shorts component, wherein
   (i) said thoracic Bolero component (101) is adapted, in use, to cover the patient's shoulders and shoulder blade area and is made of non-elastic material,
   (ii) the pelvic shorts component (110) adapted, in use, to encircle the patient's pelvis and made of elastic-material and reinforced with non-elastic materials,
   (iii) a non-elastic strapping system adapted, in use, to encircle the patient's pelvis transversely as a pelvic band (111, 112, 113, 114) attached to the pelvic shorts component (110) and providing a stable fitting, resistant to transverse plane rotations and proximal migration, and
   (iv) a minimum of four removable, corrective elastic bands (130, 130(2)A, 130(3)A, 130(4)A) adapted, in use, to run obliquely around part or all of the circumference of the patient's torso and each of said bands has a first end connected directly to said thoracic Bolero component (101) and each of said bands has a second end connected directly to said pelvic band, said corrective bands being adapted, in use, in tension and fastening position according to the specific movement required, to be applied to a segment of the torso involved in order to correct the deformity, relieve pain, improve posture and prevent progression of the deformity.

2. An orthosis as claimed in claim 1, wherein said pelvic shorts component (110) is made of an elastic material available in sizes from 20" to 50", but allows said pelvic band (111, 112, 113, 114) to be tensioned sufficiently to provide a stable anchorage for said pelvic band (111, 112, 113, 114).

3. An orthosis (100) as claimed in claim 1, made entirely of elastic and non-elastic materials.

4. An orthosis as claimed in claim 1, wherein said pelvic shorts component (110) acts as a carrier for said pelvic band (111, 112, 113, 114).

5. An orthosis as claimed in claim 1, wherein the corrective elastic bands are configured to produce a three-dimensional effect on the torso in relation to the pelvis within a sagittal plane, a frontal plane and a transverse plane of the torso.

6. The orthosis as claimed in claim 5, wherein in producing the three-dimensional effect on the torso, the orthosis changes the alignment of the spine within the sagittal plane, the frontal plane and the transverse horizontal plane of the torso.

7. The orthosis as claimed in claim 1, wherein the orthosis is configured to produce change in a sagittal plane, a frontal plane and a transverse plane of the torso.

8. The orthosis as claimed in claim 1, wherein the orthosis is configured to produce dynamic forces to produce change in postural alignment whilst still allowing near total mobility of the patient's body.

* * * * *